(12) United States Patent
Yu (10) Patent No.: US 10,959,450 B2
(45) Date of Patent: Mar. 30, 2021

(54) FOOD COMPOSITION FOR RELIEVING SYMPTOMS OF ALLERGIC AND AUTOIMMUNE DISEASES

(71) Applicant: Heong Jun Yu, Incheon (KR)

(72) Inventor: Heong Jun Yu, Incheon (KR)

( * ) Notice: Subject to any disclaimer, the term of this patent is extended or adjusted under 35 U.S.C. 154(b) by 0 days.

(21) Appl. No.: 15/959,268

(22) Filed: Apr. 22, 2018

(65) Prior Publication Data

US 2019/0110512 A1 Apr. 18, 2019

(30) Foreign Application Priority Data

Oct. 15, 2017 (KR) .................. 10-2017-0133682

(51) Int. Cl.
| | | |
|---|---|---|
| *A23L 33/105* | (2016.01) | |
| *A23L 33/15* | (2016.01) | |
| *A61K 35/644* | (2015.01) | |
| *A61K 36/8994* | (2006.01) | |
| *A61K 36/324* | (2006.01) | |
| *A61K 36/328* | (2006.01) | |
| *A61K 31/375* | (2006.01) | |
| *A61K 47/26* | (2006.01) | |
| *A23L 33/125* | (2016.01) | |

(52) U.S. Cl.
CPC .......... *A23L 33/105* (2016.08); *A23L 33/125* (2016.08); *A23L 33/15* (2016.08); *A61K 31/375* (2013.01); *A61K 35/644* (2013.01); *A61K 36/324* (2013.01); *A61K 36/328* (2013.01); *A61K 36/8994* (2013.01); *A61K 47/26* (2013.01); *A23V 2002/00* (2013.01); *A23V 2200/324* (2013.01); *A23V 2250/204* (2013.01); *A23V 2250/21* (2013.01); *A23V 2250/6422* (2013.01); *A23V 2250/708* (2013.01)

(58) Field of Classification Search
CPC ............. A61K 36/32; A61K 36/8994; A61K 2300/00; A61K 35/644; A61K 36/324; A61K 36/328; A61K 31/375; A61K 47/26; A23V 2002/00; A23V 2200/324; A23V 2250/204; A23V 2250/21; A23V 2250/6422; A23V 2250/708; A23L 33/105; A23L 33/125; A23L 33/15; A23L 21/25; A23L 33/10

USPC ................................................ 424/748, 776
See application file for complete search history.

(56) References Cited

U.S. PATENT DOCUMENTS

| | | | | |
|---|---|---|---|---|
| 6,054,143 | A * | 4/2000 | Jones ................... | A61K 9/0043 424/434 |
| 2005/0201970 | A1* | 9/2005 | Hu ....................... | A61K 9/0014 424/74 |
| 2007/0207226 | A1* | 9/2007 | Mowrey ............ | A61K 31/4439 424/762 |
| 2011/0150995 | A1* | 6/2011 | Joshi ..................... | A61K 36/00 424/474 |
| 2014/0248370 | A1* | 9/2014 | Ali ...................... | A61K 36/324 424/535 |
| 2016/0346336 | A1* | 12/2016 | Christopher ......... | A61K 9/06 |

FOREIGN PATENT DOCUMENTS

| | | | | |
|---|---|---|---|---|
| DE | 4111782 | A1 * | 10/1992 | .......... A61K 35/644 |
| EP | 0129032 | A2 * | 12/1984 | .............. A23F 5/40 |
| KR | 2017080342 | A * | 7/2017 | |

OTHER PUBLICATIONS

Inhibitory Effects of Methanol Extract of Seeds of Job's Tears (Coix Lachryma-Jobi L. Var. Ma-Yuen) on Nitric Oxide and Superoxide Production in Raw 264.7 Macrophages, Immunopharmacology and Immunotoxicology, 22, 545-554 (Year: 2000).*
Tongta et al. "Structure and Chemical and Physicochemical Properties of Job's Tear (*Coix lacryma*—Jobi" L.) Kernels and Flours(J. Science Technology 18(2): 109-122) (Year: 2011).*
Yin et al. "Protective Effect of Dietary Xylitol on Influenza A Virus Infection" (Laboratory of Virology, College of Pharmacy, Chung-Ang University, Dongiak-Gu, Seoul, South Korea) (Year: 2014).*
Watanabe et al. "Anti-influenza Viral Effects of Honey In Vitro: Potent High Activity of Manuka Honey" (Archives of Medical Research 45 (2014) 359-365) (Year: 2014).*

* cited by examiner

*Primary Examiner* — Aaron J Kosar
(74) *Attorney, Agent, or Firm* — Ryuh Patent Law; Steven Yu

(57) ABSTRACT

Disclosed is a food composition relieving the symptoms of various kinds of viral diseases or diseases suspected to be viral diseases. The food composition according to the present invention contains *coix*, xylitol, vitamin C, manuka honey, frankincense, myrrh and propolis in the form of powders, liquid or extract.

2 Claims, 2 Drawing Sheets

FOOD COMPOSITION FOR RELIEVING SYMPTOMS OF ALLERGIC AND AUTOIMMUNE DISEASES

BACKGROUND

The present invention relates to a food composition, and more particularly, to a food composition relieving symptoms of various viral diseases or suspected viral diseases.

The methods of avoiding illness and overcoming the illness are mostly the same. One way to do this is to develop immunity to pathogenic microorganisms and to eradicate pathogenic microorganisms. Pathogenic microorganisms include viruses, bacteria, fungi, *Acarus folliculorum*, and the like. Among them, viruses were not correctly identified by modern medicine. Therefore, modern medicine is not responding well to virus. The present inventor has come to assume that many diseases in which modern medicine cannot provide a proper treatment are caused by infection of viruses, and it has been confirmed that this speculation is true while applying the food composition according to the present invention to many patients. Therefore, in the future, the fight against viruses will play a key role in overcoming many diseases.

On the other hand, viruses are difficult to screen for their virulence due to their nature. It is very difficult for vaccines or therapeutic drugs to show the therapeutic effect continuously because of the easy occurrence of resistant viruses. In addition, the virus is parasitic in the host's cells, and when the host's immunity is strong, it loses its contact with the immune cells in the cell, and when the immunity of the host becomes weak, it exits the cell and exerts its virulence. Therefore, unlike bacteria or fungi, even if the virus is infected, it is difficult to confirm the pathogenicity of the virus because there are many cases in which the pathological symptoms do not appear due to the inactivity of the virus. Tuberculosis and leprosy have been mistaken for genetic diseases in times of lack of information about germs. Although some diseases are viral diseases, they are misdiagnosed as diseases caused by genetic or familial reasons because no virus was found or the virulence of the virus was not revealed.

Viruses are parasitic in living cells, small in size, simple in structure, and highly likely to mutate. There are many more types of viruses that are unknown than known types, because new types or variants continue to emerge. Since the emergence of new or variant viruses is frequent and difficult to predict, development of vaccines is difficult. With the advent of frequent variant viruses, it is often difficult for an antiviral agent developed by hard-working to continue to exert therapeutic effects.

Conventionally, different antiviral agents have been developed and applied for different types of viruses. For viral diseases such as avian influenza, severe acute respiratory syndrome, novel influenza, and Middle East respiratory syndrome coronavirus, vaccines or therapeutic agents having unique effects only on individual diseases are being developed. However, such a vaccine or a therapeutic agent does not exhibit any effect for a variant virus or a newly emerging virus.

Therefore, there is a need to develop foods that can alleviate or cure symptoms of various kinds of viral diseases or suspected viral diseases.

US Patent Application Publication No. 2004/0091555 A1 discloses a method for producing an agrimonia extract that exhibits an antiviral effect against hepatitis B virus and a food composition containing the agrimonia extract. However, the agrimonia extract is merely exert effective activities against the hepatitis B virus, there cannot be effective with other types of diseases which are suspected viral infection or viral diseases.

SUMMARY

An object of the present invention is to provide a food composition capable of alleviating symptoms of various viral diseases or suspected viral diseases.

Another object of the present invention is to provide a food composition capable of clinically alleviating the symptoms of various diseases which have been considered as incurable diseases, genetic diseases and the like.

Embodiments of the present invention provide a food composition comprising *coix*, xylitol, vitamin C, manuka honey, francincense, myrrh and propolis in the form of powders, liquid or extract.

In some embodiments, the food composition according to the present invention can be made into pill or granules by mixing manuka honey in a mixed powder of *coix*, xylitol, vitamin C, frankincense extract, myrrh and propolis extract.

In still other embodiments, the food composition according to the present invention may contain, as an active ingredient, an extract extracted from a mixture of *coix*, xylitol, vitamin C, manuka honey, frankincense, myrrh and propolis.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION OF THE EMBODIMENTS

Hereinafter, exemplary embodiments will be described in more detail with reference to the accompanying drawings.

The food composition according to the present invention contains *coix*, xylitol, vitamin C, manuka honey, frankincense, myrrh and propolis in the form of powders, liquid or extract.

The composition ratios and the inter-component composition ratios of the present invention are as follows.

i) 5 to 60% by weight of *coix* (based on total weight, the same applies hereinafter);
ii) 10 to 40% by weight of xylitol;
iii) 1 to 20% by weight of vitamin C;
iv) 1 to 20% by weight of manuka honey;
v) 1 to 20% by weight of frankincense;
vi) 1 to 20% by weight of myrrh;
vii) 0.1 to 10% by weight of propolis.

When *coix* is added in an amount of less than 5% by weight, antiviral effect by *coix* is insignificant. When *coix* is added in an amount exceeding 60% by weight, the effect of *coix* is not increased and it is difficult to make the composition effective against various kinds of viruses.

When xylitol is added in an amount of less than 10% by weight, the antiviral effect of xylitol is insignificant. When xylitol is added in an amount of more than 40% by weight, the effect of xylitol is not increased and it is difficult to make the composition effective against various kinds of viruses.

When vitamin C is added in an amount of less than 1% by weight, the antiviral effect by vitamin C is insignificant. When vitamin C is added in an amount exceeding 20% by weight, the effect of vitamin C is not increased and it is difficult to make the composition effective against various kinds of viruses.

When manuka honey is added in an amount of less than 1% by weight, the antiviral effect by manuka honey is insignificant. When manuka honey is added in an amount exceeding 20% by weight, the effect of manuka honey is not increased and it is difficult to make the composition effective against various kinds of viruses.

If frankincense is added at less than 1% by weight, the antiviral effect by frankincense is insignificant. If frankincense is added by more than 20% by weight, the effect of frankincense is not increased and it is difficult to make the composition effective against various kinds of viruses.

When myrrh is added in an amount of less than 1% by weight, the antiviral effect by myrrh is insignificant. When myrrh is added in an amount exceeding 20% by weight, the effect of myrrh is not increased and it is difficult to make the composition effective against various kinds of viruses.

Addition of less than 0.1% by weight of propolis results in insignificant antiviral effect of propolis. Addition of more than 10% by weight of propolis results in less increase of the antibacterial effect by propolis, but it is difficult to add antiviral function by other materials, so it is difficult to make the composition effective against various kinds of viruses.

The food composition according to the present invention can be made into pills or granules by mixing manuka honey and propolis in a mixed powder of *coix*, xylitol, vitamin C, frankincense and myrrh.

The food composition according to the present invention can be made into pills or granules by mixing manuka honey in a mixed powder of *coix*, xylitol, vitamin C, frankincense extract, myrrh and propolis extract.

The food composition according to the present invention may contain, as an active ingredient, an extract extracted from a mixture of *coix*, xylitol, vitamin C, manuka honey, frankincense, myrrh and propolis. Extraction can be done by mixing the mixture with water, or ethanol, or water and ethanol. The extract can be made into powders by drying or liquid without drying.

*Coix* is *Coix lacryma-jobi* L. var. *ma-yuen* Stapf's seed of which coat has been removed.

Xylitol is pentose extracted from birch bark and sap.

Vitamin C is an antioxidant that protects the body against free radicals and prevents cancer, atherosclerosis, rheumatism, and strengthens the immune system.

Manuka honey is a bee collecting honey from the flowers of Manuka tree native to New Zealand.

Frankincense is condensed and dried resin exuding from trunk and bark of *Boswellia carterii* Birdwood.

Myrrh is the dried resin from the trunk and bark of *Commiphora myrrha* Engler.

Propolis is a collection of bees' resin from trees, grasses, and flowers, mixed with their saliva and secretions.

Among these, propolis, myrrh, and frankincense have the most direct and powerful effect on the virus, regardless of their proportions. Therefore, if one of propolis, myrrh and francincense is omitted, the antiviral effect is markedly reduced. *Coix*, xylitol, vitamin C and manuka honey supplement and enhance the antiviral effects of propolis, myrrh and frankincense. The effect of the food composition according to the present invention on diseases of various kinds of viral diseases or suspected of viral diseases is due to the addition of *coix*, xylitol, vitamin C and manuka honey to increase synergy with propolis, myrrh and frankincense.

Among the constituents of the food composition according to the present invention, *coix*, xylitol, manuka honey, frankincense, myrrh and propolis are derived from natural life forms and are registered as safe natural food ingredients in the Korean Food and Drug Administration.

One of the characteristics of viral diseases is that it occurs intensively in areas, where contact with external substances such as skin and mucous membranes, is frequent. Most viruses are infected by contact, so they are frequently infected with skin or mucous membranes that are frequently in contact with external substances or objects. Viruses are difficult to penetrate directly into healthy skin, but are susceptible to infection through areas of *Acarus folliculorum* infection, inflammation sites, or areas of skin damage. The virus can easily infiltrate anywhere in the mucous membrane and can be transmitted to the inner wall of the nose, the inner wall of the bronchus, the inner wall of the mouth, the inner wall of the intestine, the inner wall of the small intestine, the inner wall of the intestine, the inner wall of the vagina. Viruses that prefer certain cells are infected only at specific sites. In the case of viruses that are friendly to certain cells, such as hepatitis B virus, they are infected only at specific sites.

Another feature of viral disease is that the symptoms are not cured and the symptoms are repeated according to their health condition. If the immune system is normal, it will survive only in the cells and will not cause any special lesions. When the immune system weakens, it infects surrounding cells and causes inherent lesions. In this way, the viral disease is repeatedly and persisted according to the immunity without symptoms clear.

Another characteristic of viral diseases is that it is difficult to find the causative virus. Bacterial diseases are easy to find causative organisms. However, in the case of a viral disease that causes a chronic disease with a weak pathogenicity, it usually hides in the cell and does not cause inflammation. If immunity is weak, it causes inflammation or sensitization of the cell. A virus can be found constantly in the same area of a patient with a weakened immune system. Therefore, the virus can be judged to be a causative virus of a specific disease. However, the virus can also be found in similar areas of normal immunocompetent people who have no experience of a specific disease. As a result, it can be classified as a virus which is not the causative virus of a specific disease and is not pathogenic. On the other hand, when a disease having the above-mentioned characteristics is assumed to be a viral disease and the food composition according to the present invention is applied, symptoms can be improved or alleviated.

Viral diseases that are already known include influenza, viral hepatitis, herpes zoster, viral conjunctivitis, infantile paralysis, AIDS, viral brain lesions, measles and mumps. In these viral diseases, there are many cases where a proper antiviral agent has not been developed yet.

Diseases that have all the characteristics of the viral diseases described above include the following; autoimmune disorder such as vitiligo, allergic diseases such as atopic dermatitis, chronic pain disorders of the musculoskeletal system, illness or development of infants, lifestyle diseases such as hypertension and diabetes, some sterility, central nervous system diseases such as developmental disorder and brain lesions, Down's syndrome, cri du chat syndrome, and muscular dystrophy, dementia.

These diseases are all considered to be viral diseases or diseases associated with viral infections.

Autoimmune disorder is a disease in which immune cells respond to certain substances in the body, but do not know exactly the cause of the disease. These diseases are persistent inflammation, such as vitiligo, rheumatism, Crohn disease, lupus, and pemphigus. These diseases are called autoimmune disorder because of the immune reaction in our body, which means constant inflammation, but no bacteria or fungi are found and the cause of inflammation is not found. Autoimmune disorder is a disease characterized by all the typical characteristics of the viral diseases described above. The present inventor speculate that the autoimmune disorder is not a disease in which an immune response occurs due to a substance in the body, causing an inflammation, but a viral infection disease in which an immune response occurs in an infected region due to a viral infection, resulting in inflammation.

Allergy and autoimmune disorder are the same diseases from the viewpoint of immune overreaction, and most of the organ specific autoimmune disorder is included in type II allergy. It is classified as allergy in which the antigen is identified, and autoimmune disorder in which the antigen is not yet known. However, the inventor of the present invention found that most of allergy including atopy is caused by a relatively weak pathogenic virus entering into a cell to sensitize the cell state. Then, an antigen as an inflammatory substance stimulates the cell to induce an immune response.

If the muscles or ligaments are damaged, such as Fibromyalgia and chronic musculoskeletal pain, the immune system is weakened and the symptoms worsen if the virus is infected before the damaged cells are completely restored. Viral inflammation is not cured cleanly, but continues with symptoms repeated. In this case, it has been confirmed through many clinical tests that the symptoms of the virus are eradicated by the food composition according to the present invention, and that the symptom is reliably improved by the appropriate strengthening exercise of the affected part.

The inventor of the present invention speculates that specific disease of childhood or failure to thrive is also a viral disease. Viral infections in young children can interfere with growth and development by causing repeated symptoms such as common cold symptoms, enlargement of the tonsils, poor growth, poor physical fitness, loss of appetite, and weakening of digestive functions. In this case, fighting the virus helps normalize the growth and development of children.

The present inventor speculates that some kinds of hypertension and diabetes are diseases associated with the virus. Type 1 diabetes is known to cause pancreatic destruction by antibodies raised after viral infection such as mumps or rubella. However, in the clinical cases of Type 1 diabetes patients, a number of examples in which the food composition according to the present invention plays a key role and reduces insulin, have been confirmed. Among the patients with type 2 diabetes mellitus and hypertension who are not well-controlled, there are many clinical cases in which the symptom is managed to a certain degree with stability only by taking the food composition according to the present invention. It is presumed that among the diabetic patients and hypertension patients, the virus may be a direct cause or secondary cause to worsen the symptoms.

The present inventor speculates that some kinds of sterility may also be diseases associated with the virus. As mentioned earlier, the mucous membrane is vulnerable to viral infection. Viral infections in the mucous membranes of the genitals can occur from time to time, and sterility can be induced if these infections become inflamed. Therefore, in the case of sterility women, it is also necessary to eradicate the virus by taking the food composition according to the present invention. Through clinical cases, we confirmed several cases of good physical fitness and good pregnancy just by eliminating the virus.

The present inventor speculates that central nerve infection symptoms such as developmental disorder and brain lesions may also be virus-related diseases. Developmental disorder is a disease that the present inventor presumes as viral central nerve infection symptoms through various clinical cases. Although it has not yet been clarified in modern medicine, developmental disorder, brain lesions and the like are presumed to be central nerve infection symptoms due to viruses, and the inventor of the present invention have experienced various clinical examples in which symptoms are improved as a result of taking the food composition according to the present invention.

The present inventor speculates that diseases that are regarded as genetic diseases in modern medicine such as Down's syndrome, cri du chat syndrome, and muscular dystrophy may also be virus-related diseases. Down's syndrome, cri du chat syndrome, muscular dystrophy and the like have been improved many times by the nerve regeneration process based on the use of the food composition according to the present invention. This repeated experience has led to the conclusion that diseases caused by viral infections are likely to be among the diseases discussed as genetic diseases.

The inventor speculates that dementia may also be a disease associated with the virus. Developmental disorder, brain lesions, etc. are presumed to be central nerve infection symptoms due to the virus, and symptoms are improved when the virus is eradicated. It is believed that the food composition according to the present invention plays a major role in the prevention and treatment of dementia.

Thus, based on our previous research and clinical experience, The inventor suspects that many diseases that have not yet been identified and that are thought to be genetic diseases will be viral diseases.

The present invention can be used in combination with a lymphatic circulation promoting food composition comprising cnidium, maple syrup, dried bigarade orange, bambusae succus, kalopanax and *coix* in the form of powders, liquid or extract.

The food composition according to the present invention is effective for alleviating symptoms of already known viral diseases such as hepatitis B, herpes zoster, adenovirus, rhinovirus, influenza, novel influenza. In addition, the food composition according to the present invention has the effect of alleviating or relieving the pathology of the following diseases suspected of being a viral disease.

1) It is presumed that the virus is infected when continuous and repeated pain is caused in the same site, such as fibromyalgia and chronic musculoskeletal pain. The food composition according to the present invention has the effect of alleviating or relieving the pain that is constantly and repeatedly caused in the same area.

2) If persistent and repeated lesions occur in the same area, such as atopic dermatitis and allergic rhinitis, it is presumed that the virus is infected. The food composition according to the present invention has the effect of alleviating or relieving the pathology in which persistent and repeated lesions are caused in the same region, such as atopic dermatitis and allergic rhinitis.

3) Most of the diseases belonging to allergy or autoimmune disorder are thought to be infections caused by viruses. The food composition according to the present invention has the effect of alleviating or relieving most diseases or pathologies belonging to allergy or autoimmune disorder.

4) Although the color of the inflammation site is slightly reddish due to inflammation, such as psoriasis, it is presumed that the virus is infected when the inflammation is maintained and the symptom severity is repeated. The food composition according to the present invention has the effect of alleviating or healing the symptoms of repeated inflammation, while the inflammation site is slightly reddish but is not easily pumped and maintained continuously.

5) Repeated and persistent chronic inflammation of the mucous membrane exposed to the outside such as eyes, nose, mouth, neck, stomach, small intestine, large intestine, female genitalia is presumed to be a viral infection. The food composition according to the present invention has the effect of relieving or healing chronic inflammation which occurs repeatedly and continuously in the eyes, nose, mouth, neck, stomach, small intestine, female genitalia.

6) Some adult diseases or life style diseases such as diabetes, hypertension, etc. are presumed to be caused by virus infection of related site. The food composition according to the present invention has the effect of alleviating or relieving symptoms such as diabetes mellitus, hypertension, or other life style disease caused by the virus.

7) Down's syndrome, cri du chat syndrome, and muscular dystrophy are also considered viral diseases of the central nervous system. The food composition according to the present invention has the effect of alleviating or relieving the symptoms of a disease, which is considered to be a genetic disease, such as Down's syndrome, cri du chat syndrome, and muscular dystrophy.

8) It is assumed that one of the causes of central nervous system diseases such as developmental disorder, brain lesions, and dementia is infection by the virus in the related site. The food composition according to the present invention has the effect of alleviating or relieving central nervous system diseases such as developmental disorder, brain lesions, dementia and the like.

Example

In order to confirm clinical effects on viral diseases, the food composition pills according to the present invention were produced several times in the following amounts.

First, a mixture of 3,200 g of *coix* powders, 2,700 g of xylitol powders, 1,200 g of vitamin C powders, 500 g of frankincense extract powders, 1,000 g of myrrh powders, and 200 g of extract powders of propolis were prepared and 1,200 g of manuka honey were further mixed. The mixture was molded into small pills having a diameter of 3-5 mm to make about 10,000 g, and these pills were packed in 4.8 g units. To obtain frankincense extract and propolis extract, frankincense and propolis were mixed with 50%-ethanol in a weight ratio of 1:30 (frankincense or propolis 1: 50%-ethanol 30, respectively). After 12 hours of extraction, the ethanol was evaporated for an appropriate period of time to remove the components of the ethanol, and the residue was removed, followed by drying and pulverization.

Since the constituent components of the present invention are all food materials known to be safe and are registered as safe food ingredients in the Korean Food and Drug Administration, they can be administered directly without any in vitro test, animal test or biomarker test. Clinical trials were carried out and the effectiveness of the study was confirmed by interviewing or observing the patients.

Clinical Trials

Clinical Trial 1—Hepatitis B (50 Years Old, Male)

A 50-year-old male patient was suffering from hepatitis B virus infection and complained of fatigue and anemic symptoms. When the virus is infected, the body causes an immune response to remove it, causing the infected hepatocytes to be destroyed, resulting in irritation and fatigue. In some cases, anemia may occur. The patient was dosed with one unit (4.8 g) of the food composition according to the present invention three times a day for three weeks and liver function test was performed. As a result, GOT and GPT levels rose sharply, but did not complain of worsening symptoms or fatigue, and anemia symptoms disappeared. This phenomenon is due to the fact that hepatocytes infected with hepatitis B virus were suddenly exposed to the food composition of the present invention and the hepatocytes infected with the virus were destroyed in the course of the virus eradication so that GOT and GPT in hepatocytes were released into the blood. After that, for 11 months, the food composition according to the present invention was appropriately added and continued to be continuously administered. After 11 months, the hepatitis B virus marker test for this patient showed no hepatitis B surface antigen (s antigen).

Clinical Trial 2—Herpes Zoster (Age 6, Female)

She was a 6-year-old girl from Beijing who had herpes zoster. The girl said she had no symptoms when she stayed in Beijing, but she had symptoms two days later when she went to her hometown. The food composition according to the present invention was dosed twice daily for two months in the morning and evening in 0.5 units. She then went back to her hometown. After two days, no herpes zoster rash was observed over a period of 7 days, and 10 days thereafter. Since then, shingles have not recurred to date.

Clinical Trial 3—Herpes Zoster (Male, 84 Years Old)

This 84-year-old man was treated with herpes zoster in a dermatologist and suffered from pain on his back and shoulders and ribs, unable to sleep at night. Herpes zoster is a disease that occurs when the chickenpox-herpes zoster virus is incubated in the body after chickenpox in childhood, and then reactivated. The virus that remains in the body migrates along the nerves and lurks in the ganglion, but when the immune system weakens, the pain in the skin causes severe inflammation. The food composition according to the invention was administered in two units (4.8 g×2) twice daily for three days, then one unit (4.8 g) three times a day for seven days. The patient stated that the pain had completely disappeared after 10 days, and the trace of herpes zoster remained only partially, but no herpes zoster was observed.

Clinical Trial 4-Herpes Zoster (36 Years, Male)

He is a 36 year old physique strong man. He has been taking prescription medicines for herpes zoster and has come to buy painkillers because he cannot sleep because of the pain. The food composition according to the present invention was dosed instead of the painkiller for three times a day, one unit at a time. The patient stated that herpes zoster remnant remained after 3 days, but the pain completely disappeared. Thereafter, the same amount of 10 days was further taken, and it was visually confirmed that the herpes zoster completely disappeared. In order to completely eliminate the latent varicella-herpes zoster virus, the food composition according to the present invention was further administered for 4 months.

Clinical Trial 5—Herpes Zoster (Age 60, Female)

This patient was a woman who suffered from herpes zoster for nearly a year in the past. The same site was sick again and received medical treatment, and the doctor ordered herpes zoster antiviral drug, Gabapentin Cap. The food composition according to the present invention was administered in two units three times a day for three days. The next day, she stated that the pain disappeared without taking the prescription medicine. The food composition according to the present invention was further administered for 6 months to completely eliminate the varicella-herpes zoster virus which is latent in the nerve cells.

Clinical Trial 6—Influenza (Male, 63 Years Old)

He was a patient taking Tamiflu against symptoms of H1N1 flu and taking it for a week. Since the improvement of symptoms due to Tamiflu was minimal, the food composition according to the present invention was administered two times a day for one week in two units. After 1 week, the symptoms improved markedly, and he was dosed with one unit three times a day for another week. Two weeks later, the patient stated that symptoms of the H1N1 flu completely disappeared.

Clinical Trial 7—Influenza (Male, 56 Years Old)

The patient was infected with the influenza B virus, complaining of high fever and systemic pain. The food composition according to the present invention was administered in two units three times a day for three days. The patient stated that symptoms were alleviated much after 3 days. After that, one unit was given twice a day for one week. The patient stated that symptoms had completely disappeared 10 days after starting dosing.

Clinical Trial 8—Sinus Cold (45 Years Old, Female)

She was a female patient who usually goes to a long cold without a cure. She was infected with rhinovirus. The food composition according to the present invention was administered in one unit three times a day for three days. The patient stated that the common cold symptom disappeared completely within three days.

Clinical Trial 9—Sinus Cold (21 Year Old Female)

She was a woman patient preparing for a qualification test. She wanted a cold medicine that did not come to sleep. The food composition according to the present invention was allowed to take one unit three times a day for six days. After completing the 2-day dose, he complained that the nasal discharge had become worse, but he continued to take it. The patient stated that her nose was cleared from the fourth day, her brain cleared, and her cold symptoms completely disappeared after 6 days of taking.

Clinical Trial 10—Sore Throat (Male, 48 Years Old)

He was a male patient with a sore throat. He was infected with adenovirus. The food composition according to the present invention was administered in one unit twice a day for three days, but the common cold symptoms did not improve because the air conditioner worked in his office with a low temperature. The food composition according to the present invention was increased in two units three times a day for an additional 3 days. The patient stated that the common cold symptoms of the neck disappeared three days later.

Clinical Trial 11—Sore Throat (40 Years Old, Female)

The patient was a 40-year-old female patient who changed day and night. She was infected with adenovirus. She had been to the hospital several times with a continuous neck swelling. She had been continuously unsatisfied because she had been suffering from ringers every time she came to the hospital. The food composition according to the present invention was allowed to take one unit three times a day for three days. The patient stated that she was much easier to get up in the morning and the cold symptoms improved much from the second day after taking the medication, and the cold symptoms completely disappeared within a week.

Clinical Trial 12—Chronic Sputum (73 Years Old, Male)

A 73-year-old man was a patient who had been taking the medicine prescribed by the hospital for more than three years because of the large amount of sputum. The food composition according to the present invention was administered in two units three times a day for 7 days. As a result, the amount of sputum was significantly reduced. This patient was given one unit twice a day for three months. After 3 months of additional dosing, the patient stated that no more sputum was produced. Most of the chronic diseases occurring in the mucous membrane are presumed to be viral diseases.

Clinical Trial 13—Psoriasis (38 Years, Male)

This patient began skin lesions eight years ago, was diagnosed with psoriasis in the hospital and has been treated continuously. There was a severe appearance of erythematous skin lesions that were characteristic of psoriasis evenly throughout the whole body skin. Initially, the food composition according to the present invention was administered in one unit three times a day for three months. After 2 weeks of taking, skin lesions filled the whole body and improved a lot after 12 weeks. After 6 months, squama and erythema were no longer visible to the naked eye. Psoriasis is a rubella skin lesion covered with a silvery white squama with a clear borderline. It is a chronic skin disorder that is likely to be repeated throughout life unless completely treated.

Clinical Trial 14—Psoriasis (Age 31, Female)

This patient had skin lesions started 20 years ago and was diagnosed as psoriasis in the hospital. There was a severe appearance of erythematous skin lesions that were characteristic of psoriasis evenly throughout the whole body skin. The food composition according to the invention was dosed in two units three times a day for 3 months. After 2 weeks, the symptoms were severe, and skin lesions filled the whole body. It was observed that erythema and squama gradually disappeared after 3-4 weeks. As a result of taking the dosage of the food composition according to the present invention for 24 months while appropriately increasing or decreasing the dose, no more erythema or squama was observed on the skin.

Clinical Trial 15—Psoriasis (55 Years, Male)

The patient went to the barbershop to get a haircut and was told by a barber that there was an erythematous skin lesion from the back scalp to the back of the neck. He was diagnosed with psoriasis in the hospital and ate prescribed medicines but did not improve. Thus, the food composition according to the invention was administered in one unit twice a day for one month. After 1 month, there was a noticeable decrease in the boundaries. After 1 month, the amount of the food composition according to the invention was increased by two units three times a day for three months. After 3 months, erythema almost disappeared and became almost indistinguishable from surrounding skin color.

Clinical Trial 16—Atopic Dermatitis (36 Years, Male)

The patient had atopic dermatitis from childhood, but the symptoms were not severe. However, during the past three years, the patient suffered from severe symptoms in the forehead, wrist, and larynx. Immediately before applying the food composition according to the present invention, symptoms were severe in the whole body. Atopic dermatitis was diagnosed in hospital. The skin is very itchy and dry, pulling, and the hard part is split, so that he cannot sleep because the symptoms are so bad. Take the hot water in the tub once a day and let the hot water come out little by little. He has had a severe atopic condition and has already retired from his job. Two units of the food composition according to the invention were taken three times a day for the first two months, and then one unit was taken three times a day for seven months. The symptoms seemed to be worse between 7-14 days after the first dose, but the treatment was continued without interruption. After 9 months, he was unable to observe atopic symptoms in his skin and stated that he no longer felt it.

Clinical Trail 17—Atopic Dermatitis (Male, 48 Years Old)

This man was a patient with severe atopic dermatitis on his face. The patient was taking antihistamines and immunosuppressants prescribed in dermatology clinics, but the symptoms were not alleviated. For this patient whose face was swollen red, the food composition according to the present invention was administered in two units three times a day for seven days. Seven days later, the reddish puffy skin became calm and the complexion returned to normal. After confirming the above effect, the food composition according to the present invention was administered in one unit three times a day for six months. After the application of the present invention, the symptoms of atopic dermatitis with redness of the face were no longer observed, and other symptoms of atopic dermatitis disappeared after 6 months of dose.

Clinical Trail 18—Atopic Dermatitis (17 Years, Female)

This patient was a 17-year-old high school girl with atopic dermatitis in the back of the knee and thigh. The food composition according to the present invention was administered in two units three times a day for 14 days. Initially, the symptoms worsened as expected, but gradually relieved. Then, the food composition according to the present invention was administered in two units twice a day for 6 months, to cure the virus causing atopic dermatitis. No symptoms of atopic dermatitis were observed in the back of the knee and in the thigh as well as other sites after 6 months of dose.

Clinical Trail 19—Vitiligo (34 Years Old, Male)

This patient had symptoms of vitiligo especially on the face, hands, and wrists, and was spread evenly throughout the body, making normal social life difficult. Especially, the lashes of the eyelids progressing with vitiligo were a few strangely white. The food composition according to the present invention was administered in two units three times a day for 24 months. After 24 months of observation, the symptoms (white spots) of vitiligo were mostly disappeared from the skin but the eyebrows that had turned white remained intact. The exact cause of vitiligo is unknown, but it is an acquired de-pigmentation disease in which various sizes of white spots appear on the skin due to the destruction of melanocytes. Vitiligo is a disease that is difficult to treat completely, although various methods are tried to treat it. Although it is not a typical form of inflammation caused by viruses, it is assumed that melanocytes are infected with a virus. Therefore, the healing process of vitiligo is to eradicate the cause virus first. It is then necessary to maintain the skin environment so that the melanocytes settle. Then, when the healing process is almost finished, the white spots become normal skin color, and at the same time, the surrounding black skin turns to the skin color. Healing of vitiligo requires 12-24 months of treatment and the improvement effect does not appear at the beginning, but it starts to appear when the healing is almost finished.

Clinical Trail 20—Chronic Rhinitis (40 Years Old, Female)

A 40-year-old woman suffered chronic rhinitis, which caused the nasal mucosa to swell all the time. The food composition according to the present invention was administered in one unit twice a day for 12 weeks. From the third week, breathing became easier, the mucous membrane of the cochlea was noticeably reduced, the nose began to feel more comfortable, and after 12 weeks the patient stated that he no longer felt chronic rhinitis. The sinuses and airways are areas that are exposed to the outside air and are susceptible to infection because they are easily exposed to viruses and germs.

Clinical Trail 21—Throat Discomfort (60 Years Old, Female)

The patient was uncomfortable and ill for six months or more as if his throat was constantly tightened. This patient was tested at the hospital to see if there was a lump in his neck, but no lump was found. There was no improvement in symptoms even after 2 months of treatment at ENT. Thus, the food composition according to the present invention was administered in one unit three times a day for 20 days. Twenty days later, the patient stated that the uncomfortable symptoms of the neck disappeared and he slept comfortably. It was very likely that it was a viral infection of the neck mucosa.

Clinical Trail 22—Chronic Gastritis (54 Years, Female)

This patient is a female pharmacist, suffering from chronic gastritis with indigestion and dyspepsia for a long time. The food composition according to the invention was administered in one unit twice a day for 4 weeks. The patient stated that postprandial dyspepsia symptoms had disappeared from 2 weeks after taking, and that no more symptoms of chronic gastritis appeared. The gastric mucosa is a site where food enters directly from the outside, and is vulnerable to invasion of the virus like nasal mucosa or airway. Therefore, if gastrointestinal diseases such as gastric atony, chronic gastritis and gastric ulcer are repeatedly maintained without cleansing, it is necessary to suspect infection by virus.

Clinical Trail 23—Allergy (55 Months, Male)

This patient was a 55-month-old boy. This patient had a lot of food allergy from birth (apple peel, peach, plum, fruit, shrimp, crustaceans, shellfish, eggs, nuts, etc.) In addition, the patient had persistent allergic rhinitis and rubbed his eyes frequently due to allergic conjunctivitis. The food composition according to the present invention was ground in a blender by one unit, and then was administered in one unit twice a day with yogurts for 3 days. Three days after eating, the inflammatory nasal mucus turned into a clear runny nose. At present, allergy is known as a viral disease.

Clinical Trail 24—Fibromyalgia (Age 59, Female)

The patient was a chronic pain patient who complained that his back, shoulders, arms, and legs were aching, tingling and sagging, and that the whole body was sore. In the evening, she said she was weary and exhausted. The food composition according to the present invention was administered in one 1 unit twice a day for 4 weeks. From the third day of taking this patient, she stated that her body became lighter and her pain began to disappear, and at any moment there was no stress, no sore. The patient was suspected of having been infected with various parts of the body.

Clinical Trail 25—Chronic Finger Pain (58 Years Old, Male)

This patient had a suture operation with the first knot of the right thumb being bitten by his wife one month ago, but there was no suppuration at the operation site, but the pain of piercing occurred, and the wrist and shoulder also had severe muscle aches. Eight years ago, he was bitten by his wife on the same finger, and he was treated with 80 needles. The pain continued for one month and the absence of suppuration was considered to be a viral infection, and the food composition according to the present invention was administered in one unit twice a day for 4 weeks. The patient stated that after 4 weeks the pain and myalgia remained clear. After the pain and myalgia had disappeared, he was given the same dose for 5 months to cure the virus radically.

Clinical Trail 26—Hypertension (Male, 53 Years)

This patient was a 53-year-old man with hypertension who complained that his blood pressure was too low to become unstable and dizziness when he took his blood pressure medicine. This patient was dosed with one unit of the food composition according to the present invention twice a day for three months. Three months later, the patient was kept in a state in which the measured blood pressure dropped to about 121 mmHg in systolic blood pressure and 81 mmHg in diastolic blood pressure without taking a blood pressure medicine. Hypertension is a typical lifestyle disease and is a typical disease that is caused by irritating food, obesity, lack of exercise, excessive stress, and the like. Although the inventor did not initially consider hypertension as a viral disease, through the clinical example in which the blood pressure was controlled by taking the food composition according to the present invention, was convinced that a virus infection can cause blood pressure in certain parts of the body by inflammation.

Clinical Trail 27—Type 1 Diabetes (42 Years, Female)

This patient was a patient with severe plantar pain due to severe diabetes. The patient's soles were so painful as to be stuck with dozens of needles in the morning, so he could not sit on the floor without rubbing his foots for more than an hour to be able to walk. His diabetes was type 1 diabetes that developed after severe acute pancreatitis. At that time, insulin was injected in the morning and evening, and the blood glucose level did not fall below 200 mg/dl. The thirst was so severe that the tongue was broken and the cold water was not cool, so the beer had to be frozen in the freezer or chewed to the ice to relieve the thirst. This patient was given no cold water, only warm water than body temperature, and spicy food was forbidden. He was regulated the week so that the thirst and blood sugar began to stabilize. This means that the cold stimulus triggers the excitement of the sympathetic nervous system, thereby increasing the blood sugar level and leading to thirst. Thereafter, the food composition according to the present invention was administered appropriately (2 units, twice a day for 3 months), so that insulin injections were reduced to 5 units in the morning only. The patient stated that the pain of the foot part disappeared in the course of taking the food composition according to the present invention, and the inflammation of the foot part was also gradually decreased. This was because the food composition according to the present invention eradicated the virus causing inflammation of the beta cells of the pancreas. Reduced insulin doses are evidence that beta cells in the pancreas are regenerating and active. Diabetes mellitus, like hypertension, is a typical lifestyle-related illness that is caused by irritating food, obesity, lack of exercise, and excessive stress. Although the inventor did not think of diabetes as a viral disease at first, the inventor have experienced a clinical case in which blood glucose is controlled by taking the food composition according to the present invention, and have found that the diabetic virus causes inflammation in specific parts of the body, raising blood sugar.

Clinical Trail 28—Sterility (31 Years Old, Female)

The patient had a one-year leave to work to treat sterility and wanted sterility treatment in earnest. However, in reality, her physical strength is so weak that even a light daily life is difficult, and she was eager to strengthen her physical strength rather than wanting her pregnancy. In the case of female sterility, if there is no specific cause for obstetrician diagnosis, female genitalia is infected with virus infection and is not pregnant. In addition, there are many cases, in which there is no extra strength to maintain the pregnancy state due to depletion of the physical strength. Thus, the inventor recommended to her a method of healing that would eliminate the virus and raise enough physical strength to become pregnant, and the patient accepted it. Ultrasonography revealed that her uterus was not clean. The food composition according to the present invention was administered in a controlled manner for a total of 12 months, and the pregnancy was attempted after 12 months. She was pregnant the very week, gave her first child a healthy birth without any problems, and then gave birth to her second child after 22 months without further care.

Clinical Trail 29—Virus Progressive Brain Lesions (9 Year Old Male)

He had convulsion for a high fever suddenly, and was diagnosed with progressive brain lesions due to the virus at Medical Center and was taking epilepsy drug. The symptoms were accompanied by a decrease in cognitive ability and athletic ability, and an occasional minor seizure. The present inventor has had experience in helping the mother of the patient to clean up atopic dermatitis that has been suffering for over 20 years. In this case, since the patient was already diagnosed with a brain disease caused by viruses, the food composition according to the present invention was taken in a proper manner for 24 months in order to eliminate the virus. Although the epilepsy drug was discontinued, the epileptic symptoms did not occur, and intelligence and athletic ability were restored to normal. Also, after 23 months, it was confirmed that the periodical brain test conducted by Medical Center no longer showed a viral infection site.

Clinical Trail 30—Brain Lesions (7 Years, Female)

This patient is a girl diagnosed with intellectual disability grade 2. The intellectual disability was reported as viral brain lesions of the central nervous system, and the food composition according to the present invention was administered for 24 months while increasing or decreasing the dose. At first, she could not walk properly, had to hold other's hand around to stand up, she could not speak, she could not communicate emotions or communicate with other. Now she is running, she is running with two feet together, she acts charming, and she is growing up as a normal child. In this case, it is judged that the virus causing the inflammation of the central nervous system was killed by the food composition according to the present invention. Central nervous system disorders such as intellectual disabilities, developmental disorders, developmental delays, depression, Attention Deficit Hyperactivity Disorder (ADHD), insomnia, panic disorder, and obsessive-compulsive disorder, as well as viral brain lesions may be diseases caused by the invasion of virus into the central nervous system.

Clinical Trail 31—Developmental Disability (4 Years, Male)

He was a patient managed by Seoul Medical Center Children's Mental Health Development Clinic. The results of psychological education test conducted by Seoul Medical Center were that actual age was 3 years 2 months, life age was 16 months, and developmental index (DQ) was 42.1. For reference, the development index (DQ) is similar to IQ, and the standard is 100. If it is 100 or more, it is considered to be ahead of development, and if it is below 100, development is delayed. In addition, it was difficult for him to perform tasks in a structured environment, such as following language instruction and sitting, and he was limited in imitating the language and behavior of others, or in performing items requiring challenges or repetition. The patient was administered with the food composition according to the present invention at a controlled dose, for about 24 months. As a result, in the progress report of the psychological education test, the actual age was 4 years and 5 months, life age was 4 years and 1 month, and development index (DQ) was 92.5. In addition, it is possible to concentrate on the task by keeping sitting for a certain period of time, and to improve the basic social skills necessary for interaction with other people such as imitation and language expression, perception, small muscle, large muscle, hand-eye coordination.

Clinical Trail 32—Muscular Dystrophy (Male, 5 Years Old)

He was a Chinese child living in Beijing. He has been diagnosed with progressive muscular dystrophy and has traveled for treatment all over China for more than six years. Before healing by the food composition according to the present invention, it was difficult to walk about 30-50 meters because of a poor growth state, and had to rest and walk again. To climb up the bed, he could not climb his hands because he had no strength in his hands. He was climbing his head to bed first. He could not sit in kindergarten, so he could not participate in class and he could not get along with other children, so he played separately. When the inventor touched his legs, there was no flesh under his knees, only the bones were raised, and the muscles that were a little in the calves were as hard as the stones, and the buttocks were a little stiffened. The height was also 82 centimeters, smaller than the other children. The food composition according to the present invention was taken for 7 months while increasing or decreasing the dose. After seven months, he could walk for a few minutes, clap his hands, climb on the bed, sit in class in kindergarten, and join classes. The legs are normal in the hip muscles and the muscles in the calves are much more common. In addition, under the muscles of the calf, the stone has been hardly touched, but has yet to show a sense of unreasonableness. Miraculously, before taking the food composition according to the invention, the height was 82 centimeters smaller than its peers, but in just seven months after it increased to 109 centimeters and was taller than the other children. Muscular dystrophy is a hereditary, progressive myopathy that has been known to cause progressive atrophy and muscle weakness, and there are no specific treatments to date. However, it has been confirmed that muscular dystrophy could be improved by the food composition according to the present invention.

Clinical Trail 33—Cri Du Chat Syndrome (5 Years, Female)

Cri du chat syndrome is a congenital disorder caused by a chromosomal abnormality, of which major symptom is crying similar to a cat's crying. The cri du chat syndrome was first reported in 1963 and appears because part of the 5th chromosome is cut off and becomes an obstacle to development and incomplete laryngeal development. Symptoms include crying similar to a cat's crying, microcephaly, and intellectual disabilities. Other symptoms include round face, wide eyelid, myasthenia gravis, palpitations, flat feet, short neck, etc. About 20% have congenital heart disease. As the patient get older, the patient can gradually lose cat's crying, myasthenia, rounded face. There is no special treatment yet. This patient, before he was not administered with the food composition according to the present invention, was separate from other people, and was in a state of being smaller than the 2-year-old younger brother and having less weight. The food composition according to the present invention was taken for 24 months while appropriately increasing or decreasing the dose. After the start of taking the food composition according to the present invention his good growth appeared, 24 months later, his height was taller than his brother and weigh out a lot of clothes so that we cannot dress the same size. Now, if other people ask him to take a picture, he takes a pose and gets along well with others. From this, it was confirmed that cri du chat syndrome is a treatable disease and also a viral disease.

Clinical Trail 34—Down's Syndrome (12 Years, Female)

Down's syndrome is a typical genetic disorder that causes mental retardation, somatic anomalies, systemic dysfunction, and growth disorders due to the presence of two chromosomes with a normal number of 21. Newborn babies have a small head since childhood, and a complex facial anomaly such as a round, flat facial nose with a low nose, a raised eye tail, and a long distance between the eyes. Throat looks short and thick, muscles are weak. The development is delayed until the age of 2 to walk, and the speech is delayed, eventually grow into adults, the average intelligence is about 20~50 IQ. The height does not grow well, so adults are small in height and are often observed as obesity. This patient was a patient who applied the food composition according to the present invention for 2 years to ascertain whether the food composition according to the present invention can cure Down's syndrome. The typical Down's syndrome was shown in this patient, and the intelligence level was so low as to talk about the grade and class of last year if asked about the grade and class of this year. The food composition according to the present invention was administered for 24 months, while the dosage was appropriately increased or decreased. It has been confirmed that symptoms have improved in just four months after starting taking it. One of the characteristics of Down's syndrome is that the forehead, nose, and lips are in a straight line. After 4 months, it is confirmed that the jaw is in place and that the forehead, nose, and lips are not in a straight line, but that their noses come out. It is thought that the jaw has returned to normal with the decrease of cerebral edema. In patient of Down's syndrome the jaw is pushed out by the cerebral edema. In the process, the shoulders and necklines were reduced, and at the same time, the fingers were seen to grow particularly. This is thought to be the result of the change of the blood current from the shoulders and the head to the limbs. Down's syndrome patient's fingers are short and the thickness of the fingers decreases sharply with the fingertips. The fingertips showed the same shape as the frog feet as the fingertips swelled round. After 24 months, the level of intelligence developed so much that she could talk to her grandmother who was a guardian and to nag her. This suggests that Down's syndrome induces viral central nervous system, resulting in a variety of external physical changes.

Manufacturing and Sales

The food composition according to the present invention was manufactured in the following composition ratios and packing units.

First, a mixture of 32 wt % of *coix* powders, 27 wt % of xylitol powders, 12 wt % of vitamin C powders, 5 wt % of frankincense extract, 10 wt % of myrrh powders and 2 wt % of propolis extract is prepared. The mixture was molded into small pills having a diameter of 3.8 mm, lyophilized, and packed in a stick pack of 4.8 g.

Figure 1:
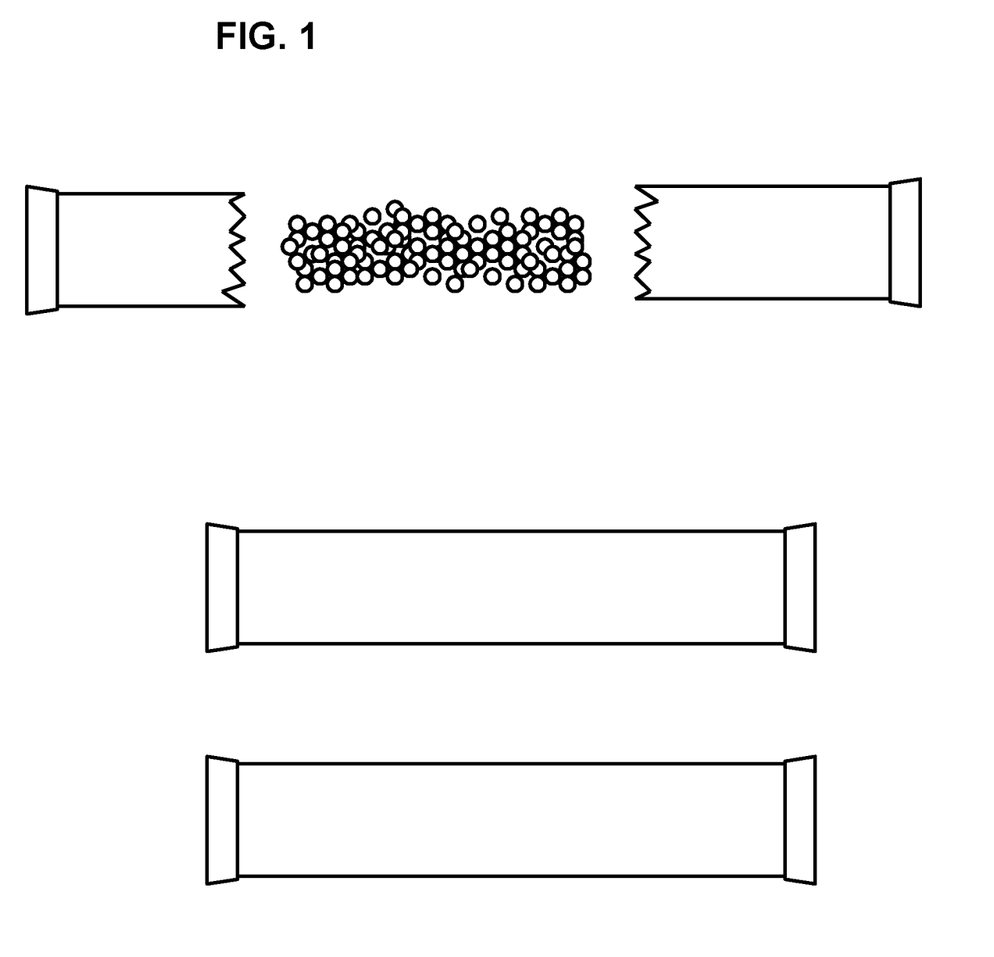
FIG. 1 is a photograph of the contents of a product of a food composition according to the present invention.
Figure 2:
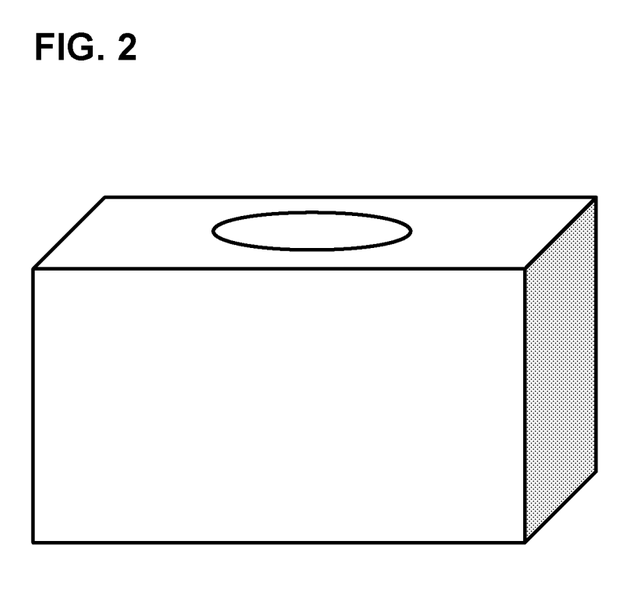
FIG. 2 is a photograph of the product package of the food composition according to the present invention.

FIG. 1 is a photograph of the product contents of the food composition according to the present invention, and FIG. 2 is a photograph of the product packaging of the food composition according to the present invention.

More than 5,800,000 stick packs (4.8 g per stick pack) were sold at 2,000 pharmacies in Korea from May 1, 2017 to Mar. 31, 2017. Through the pharmacists who participated in the sales, the following symptom improvement effects were confirmed.

1) The results of treatment with 1,000 influenza patients were followed up, and the symptom improvement effect was confirmed in 970 patients (97%).

2) The results of the administration of 500 patients with sinus cold (rhinovirus) were followed up, and 450 patients (90%) showed symptom improvement.

3) The results of 100 patients with herpes zoster were followed up, and 95 patients (95%) showed improvement of symptoms.

4) The results of 100 patients with atopic dermatitis were followed up, 93 patients (93%) showed improvement of symptoms.

5) The results of 300 chronic rhinitis patients were followed up, 285 patients (95%) showed improvement of symptoms.

6) The results of 100 patients with psoriasis were followed up, 92 patients (92%) showed improvement of symptoms.

What is claimed is:

1. A food product for relieving symptoms of allergic or autoimmune diseases, comprising:
    a packet;
    contained in the packet, multiple pills that each have a diameter of 3-5 mm, each pill comprising a mixture of:
    about 32 wt % of *coix* powder;
    about 27 wt % of xylitol;
    about 12 wt % of vitamin C powder;
    about 5 wt % of frankincense extract;
    about 10 wt % of myrrh powder;
    about 2 wt % of propolis extract;
    wherein the food product is effective in treating atopic dermatitis, chronic rhinitis, or psoriasis.

2. The food product of claim 1, wherein the total weight of the multiple pills in the packet is about 4.8 grams.

* * * * *